United States Patent [19]

de la Burde et al.

[11] 4,340,073

[45] Jul. 20, 1982

[54] EXPANDING TOBACCO

[75] Inventors: Roger Z. de la Burde, Powhatan; Patrick E. Aument, Hopewell, both of Va.

[73] Assignee: Philip Morris, Incorporated, New York, N.Y.

[21] Appl. No.: 441,767

[22] Filed: Feb. 12, 1974

[51] Int. Cl.³ .............................................. A24B 3/18
[52] U.S. Cl. ................................... 131/291; 131/294; 131/295; 131/296; 131/900
[58] Field of Search ............... 131/140, 291, 296, 297, 131/309, 900; 426/445, 446, 447, 448, 449, 450

[56] References Cited

U.S. PATENT DOCUMENTS

| | | | |
|---|---|---|---|
| 1,789,435 | 1/1931 | Hawkins | 131/140 P |
| 1,924,827 | 8/1933 | Anderson | 426/448 |
| 3,575,178 | 4/1971 | Stewart | 131/140 P |
| 3,665,061 | 5/1972 | Eberly | 131/140 P |
| 3,771,533 | 11/1973 | Armstron et al. | 131/140 P |

Primary Examiner—V. Millin

Attorney, Agent, or Firm—Arthur I. Palmer, Jr.; George E. Inskeep

[57] ABSTRACT

A process for expanding tobacco is provided which employs liquid carbon dioxide as the expansion agent. Tobacco is contacted with liquid carbon dioxide to thoroughly impregnate the tobacco with the liquid carbon dioxide. The carbon dioxide impregnated tobacco is maintained at a temperature no lower than $-2°$ C. and under conditions of temperature and elevated pressure such that all or substantially all of the carbon dioxide which is in contact with the tobacco is in liquid form. After the impregnation has been completed, any excess liquid carbon dioxide which may be present with the tobacco may be removed from the tobacco. The elevated pressure is then reduced in order to convert the liquid carbon dioxide to solid carbon dioxide within the tobacco structure. The resulting solid carbon dioxide-containing tobacco is then subjected to conditions of temperature and pressure, preferably by rapid heating at atmospheric pressure, such that the solid carbon dioxide is vaporized and the tobacco is thereby expanded. Apparatus for carrying out the above described process is also provided.

17 Claims, 6 Drawing Figures

EXPANDING TOBACCO

BACKGROUND OF THE INVENTION

The tobacco art has long recognized the desirability of expanding tobacco to increase the bulk or volume of tobacco. There have been various reasons for expanding tobacco. One of the early purposes for expanding tobacco involved making up the loss of weight caused by the tobacco curing process. Another purpose was to improve the smoking characteristics of particular tobacco components, namely tobacco stems. It has also been desired to increase the filling power of tobacco so that a smaller amount of tobacco would be required to produce a smoking product, such as a cigarette, which would have the same firmness and yet would produce lower tar and nicotine than the comparable smoking product made of non-expanded tobacco having a more dense tobacco filler.

Various methods have been proposed for expanding tobacco, including the impregnation of tobacco with a gas under pressure and the subsequent release of the pressure, whereby the gas causes expansion of the tobacco cells to increase the volume of the treated tobacco. Other methods which have been employed or suggested have included the treatment of tobacco with various liquids, such as water or relatively volatile organic liquids, to impregnate the tobacco with the same, after which the liquids are driven off to expand the tobacco. Additional methods which have been suggested have included the treatment of tobacco with solid materials which, when heated, decompose to produce gases which serve to expand the tobacco. Other methods include the treatment of tobacco with gas-containing liquids, such as carbon dioxide-containing water, under pressure to incorporate the gas in the tobacco and when the tobacco impregnated therewith is heated or the pressure thereon is reduced to thereby expand the tobacco. Additional techniques have been developed for expanding tobacco which involve the treatment of tobacco with gases which react to form solid chemical reaction products within the tobacco, which solid reaction products may then decompose by heat to produce gases within the tobacco which cause expansion of the tobacco upon their release. More specifically:

A patent to Wilford J. Hawkins, U.S. Pat. No. 1,789,435, granted in 1931, describes a method and apparatus for expanding the volume of tobacco in order to make up the loss of weight caused in curing tobacco leaf. To accomplish this object, the cured and conditioned tobacco is contacted with a gas, which may be air, carbon dioxide or steam under pressure and the pressure is then relieved, whereby the tobacco tends to expand. The patent states that the volume of the tobacco may, by that process, be increased to the extent of about 5-15%.

An alien property custodian document No. 304,214 to Joachim Bohme, dated 1943, indicates that tobacco can be expanded using a high frequency generator but that there are limitations to the degree of expansion which can be achieved without affecting the quality of the tobacco.

A patent to Frank J. Sowa, U.S. Pat. No. 2,596,183, granted in 1952, sets forth a method for increasing the volume of shredded tobacco by adding additional water to the tobacco to cause the tobacco to swell and thereafter heating the moisture containing tobacco, whereby the moisture evaporates and the resulting moisture vapor causes expansion of the tobacco.

A series of patents to Roger Z. de la Burde, one of the present coinventors, granted in 1968, specifically U.S. Pat. Nos. 3,409,022, 3,409,023, 3,409,027 and 3,409,028, relate to various processes for enhancing the utility of tobacco stems for use in smoking products by subjecting the stems to expansion operations utilizing various types of heat treatment or microwave energy.

A patent to John D. Hind, granted in 1969, U.S. Pat. No. 3,425,425, which is assigned to the same assignee as the assignee of the present invention, relates to the use of carbohydrates to improve the puffing of tobacco stems. In that process, tobacco stems are soaked in an aqueous solution of carbohydrates and then heated to puff the stems. The carbohydrate solution may also contain organic acids and/or certain salts which are used to improve the flavor and smoking qualities of the stems.

A publication in the "Tobacco Reporter" of November 1969 by P. S. Meyer describes and summarizes tobacco puffing or expansion procedures or investigations for expanding and manipulating tobacco for purposes of reducing costs and also as the means for reducing the "tar" content by reduction in the delivery of smoke. Mention is made in this publication of puffing tobacco by different procedures including the use of halogenated hydrocarbons, low pressure or vacuum operation, or high pressure steam treatment that causes leaf expansion from inside the cell when outside pressure is suddenly released. Mention is also made in this publication of freeze-drying tobacco which can also be employed to obtain an increase in volume.

Since the above-mentioned "Tobacco Reporter" article was published, a number of tobacco expansion techniques, including some of the techniques described in the article, have been described in patents and/or published patent applications. For example:

U.S. Pat. No. 3,524,452 to Glenn P. Moser et al and U.S. Pat. No. 3,524,451 to James D. Frederickson, both issued in 1970, relate to the expansion of tobacco using a volatile organic liquid, such as a halogenated hydrocarbon.

U.S. Pat. No. 3,734,104 to William M. Buchanan et al, which is assigned to the same assignee as the assignee of the present invention, issued in 1973, relates to a particular process for the expansion of tobacco stems.

U.S. Pat. 3,710,803 to William H. Johnson, issued in 1973 and British Specification No. 1,293,735 to American Brands Inc., published in 1972, both relate to freeze drying methods for expanding tobacco.

South African application Nos. 70/8291 and 70/8292 to R. J. Reynolds Tobacco Company, both issued in 1970, relate to tobacco expansion employing chemical compounds which decompose to form a gas or with inert solutions of a gas under pressure to maintain the gas in solution until it impregnates the tobacco.

A patent to Robert G. Armstrong et al, U.S. Pat. No. 3,771,533, issued in 1973, which is assigned to the same assignee as the assignee of the present invention, involves a treatment of tobacco with carbon dioxide and ammonia gases, whereby the tobacco is saturated with these gases and ammonium carbonate is formed in situ. The ammonium carbonate is thereafter decomposed by heat to release the gases within the tobacco cells and to cause expansion of the tobacco.

Despite all of the above-described advances in the art, no completely satisfactory process has been found.

The difficulty with the various earlier suggestions for expanding tobacco is that, in many cases, the volume is only slightly or at best only moderately increased, noting for example, the 15% expansion as the maximum achieved by freeze drying, this type of operation has the disadvantages of requiring elaborate and expensive equipment and very substantial operating costs. With respect to the teaching of using heat energy, infrared or radiant microwave energy to expand tobacco stems, the difficulty is that while stems respond to these heating procedures, tobacco leaf has not generally been found to respond effectively to this type of process.

The use of special expanding agents, for example, halogenated hydrocarbons, such as are mentioned in the Meyer publication for expanding tobacco, is also not completely satisfactory because these substances are generally required to volatilize or remove the substances after the tobacco has been expanded. The introduction, in considerable concentration, of materials which are foreign to tobacco presents the problem of removing the expansion agent after the treatment has been completed in order to avoid affecting aroma and other properties of the smoke due to extraneous substances used or developed from the combustion of the treated tobacco.

The use of solid chemicals to produce a gas upon decomposition has not been found satisfactory, perhaps due to the fact that the chemicals cannot be incorporated in the cells of the tobacco.

The use of carbonated water has also not been found to be effective.

While the method employing ammonia and carbon dioxide gases is an improvement over the earlier described methods, it is not completely satisfactory and can result, under some circumstances, in undesired deposition of ammonium carbonate during the process.

The present process employing liquid carbon dioxide, as described hereinafter, has been found to overcome the disadvantages of the prior art processes and provides an improved method for expanding tobacco.

Carbon dioxide has been used in the food industry as a coolant and, more recently, has been suggested as an extractant for food flavors. It has also been described in German Offenlegungsschrift No. 2,142,205 (Anmeldetag; Aug. 23, 1971) for use, in either gaseous or liquid form, to extract aromatic materials from tobacco. However, there has been no suggestion, in connection with these uses, of the use of liquid carbon dioxide for the expansion of these materials.

SUMMARY OF THE INVENTION

A process for expanding tobacco is provided which employs liquid carbon dioxide as the expansion agent. Tobacco is contacted with liquid carbon dioxide to thoroughly impregnate the tobacco with the liquid carbon dioxide, preferably under conditions whereby the moisture in the tobacco is not permitted to freeze. The carbon dioxide impregnated tobacco is maintained at a temperature no lower than about −2° C. and under condition of temperature and elevated pressure such that all or substantially all of the carbon dioxide which is in contact with the tobacco is in liquid form. After the impregnation has been completed any excess liquid carbon dioxide which may be present with the tobacco may be removed from the tobacco. The elevated pressure is then reduced in order to convert the liquid carbon dioxide to solid carbon dioxide within the tobacco structure. The resulting solid carbon dioxide-containing tobacco is then subjected to conditions of temperature and pressure, preferably rapid heating at atmospheric pressure, which result in the vaporization of the solid carbon dioxide and the consequent expansion of the tobacco to provide a tobacco of lower density and increased volume.

Apparatus for carrying out the above described process also is provided such apparatus including a pressure vessel in which the impregnation of the tobacco is effected, the pressure vessel being provided with devices for controlling the admission and withdrawal therefrom of tobacco and liquid carbon dioxide, venting of the vessel to convert the liquid carbon dioxide to solid carbon dioxide and optionally means for effecting vaporization of the solid carbon dioxide to effect tobacco expansion.

DETAILED DESCRIPTION OF THE INVENTION

The present invention relates broadly to a process for expanding tobacco employing a readily available, relatively in-expensive, non-combustible and non-toxic expansion agent and more particularly to the production of an expanded tobacco product of substantially reduced density produced by impregnating tobacco under pressure with liquid carbon dioxide, converting the liquid carbon dioxide to solid carbon dioxide in situ, which may be accomplished by rapidly releasing the pressure, and thereafter causing the solid carbon dioxide to vaporize and expand the tobacco, which may be accomplished by subjecting the impregnated tobacco to heat, radiant energy or similar energy generating conditions which will cause the solid carbon dioxide which is in the tobacco to rapidly vaporize.

To carry out the process of the invention, one may treat either whole cured tobacco leaf, tobacco in cut or chopped form, or selected parts of tobacco such as tobacco stems or maybe reconstituted tobacco. In comminuted form, the tobacco to be impregnated may have a particle size of from about 20 to 100 mesh, but is preferably not less than about 30 mesh. The material treated may be in relatively dry form, or may contain the natural moisture content of tobacco or even more. Generally, the tobacco to be treated will have at least about 8% moisture (by weight) and less than about 50% moisture.

The tobacco will generally be placed in a pressure vessel in a manner whereby it can be suitably immersed or contacted by liquid carbon dioxide. For example, a wire cage or platform may be used.

The tobacco-containing pressure vessel is preferably then purged with carbon dioxide gas, the purging operation generally taking from about 1 to 4 minutes. The purging step may be eliminated without detriment to the final product. The benefits of purging are the removal of gases that interfere with a carbon dioxide recovery process and to flush foreign gases that may interfere with full penetration of the liquid carbon dioxide.

The liquid carbon dioxide which is employed in the process of this invention will generally be obtained from a storage vessel where it is maintained at a pressure of from about 215 to 305 psig and temperatures of from −20° to 0° F. (−29° to 18° C.) The liquid carbon dioxide may be introduced into the pressure vessel at 215 to 320 psig and −20° to 0° F. (−29° to 18° C.), but is preferably preheated, for example, by suitable heating coils around the feed line, to a temperature of about 0° to 25° C., and a pressure of about 490 to 906 psig before being introduced into the pressure vessel. Preheating is preferred because the best operational pressure occurs in the range of 600 to 900 psig and preheating will minimize the heating cycle in the pressure vessel. At the time the liquid carbon dioxide is introduced into the pressure vessel, the interior of the vessel, including the tobacco to be treated, will generally be at a temperature of 0° to 25° C. and pressure at least sufficient to maintain the carbon dioxide in a liquid state.

The liquid carbon dioxide is introduced into the vessel in a manner which permits it to completely contact the tobacco and sufficient liquid carbon dioxide is employed to completely saturate the tobacco. Generally this will comprise using about 1 to 10 parts by weight of liquid carbon dioxide per part of tobacco. Excess liquid carbon dioxide will be wasteful but will work. The temperature of the tobacco, during the contact with liquid carbon dioxide, should be at least −2° C. and should be no higher than 31° C. While the inventors do not wish to be bound by any particular theory, they believe that the conditions of contact between the tobacco and liquid carbon dioxide, under the present invention, are such that the unbound moisture in the tobacco is not frozen after contact, as this would prevent proper saturation of the tobacco by the carbon dioxide, and that the temperature of the tobacco in the vessel be maintained at a level of −2° C. or above or be brought to that level within 2 to 4 minutes after the introduction of the carbon dioxide to the tobacco. Thus, it is believed that it is desirable to have conditions whereby there is simultaneous retention of all or substantially all of the unbound moisture which is present in the tobacco in liquid form. It is believed that by maintaining conditions such that ice is not formed while the liquid carbon dioxide is in contact with the tobacco, adequate penetration of the tobacco by the liquid carbon dioxide is ensured. The temperature of the liquid carbon dioxide should not, during this impregnation step, be permitted to exceed about 31° C., since it must be in its liquid condition to be effective.

The pressure during the contacting step is preferably maintained at about 600 to 900 psig by heating the vessel, using heating coils or the like.

The tobacco and carbon dioxide may be maintained in contact under these conditions for a period of 0.5 to 60 minutes.

After the liquid carbon dioxide has been permitted to saturate the tobacco, generally for a total period of from about 0.5 to 60 minutes and preferably from about 2 to about 4 minutes, any excess liquid carbon dioxide which may be present is drained out of the vessel, preferably while maintaining the conditions of temperature and pressure at the same levels as during the contacting step.

The pressure in the vessel is then released, by venting the gases in order to bring the contents of the vessel to atmospheric pressure. This venting should require from 0.75 to 50 minutes, depending on the size of the vessel, but should preferably take no longer than 3 minutes, after which the temperature in the vessel will be from about −85° to −95° C. and the liquid carbon dioxide in the tobacco will be converted to solid carbon dioxide. The pressure need not be reduced to atmospheric, but need only be reduced below about 60 psig. Obviously, this is not as preferable from a commercial viewpoint.

After the carbon dioxide in the tobacco is converted to its solid form, the solid carbon dioxide-containing tobacco is then exposed to expansion conditions by subjecting the treated product to heat or the equivalent in order to vaporize and remove the solid carbon dioxide from the tobacco. This may comprise the use of hot surfaces, or a stream of hot air, a mixture of gas and steam, or exposure to other energy sources such as radiant microwave energy or infrared radiation. A convenient means of expanding the solid carbon dioxide-containing tobacco is to place it or to entrain it in a stream of heated gas, such as superheated steam or to place it in a turbulent air stream maintained, for example, at a temperature of from about 150° to about 260° C. (as low as 100° C. and as high as 370° C.) for a period of about 0.2 to 10 seconds. The impregnated tobacco may also be heated by being placed on a moving belt and exposed to infrared heating, by exposure in a cyclone dryer, by contact in a tower with superheated steam or a mixture of steam and air or the like. Any such contacting steps should not raise the temperature of the atmosphere with which the tobacco is in contact to above about 370° C. and should preferably be from at about 100° C. to about 300° C., most preferably 150° C. to 260° C. when conducted at atmospheric pressure.

As is well known in processing of any organic matter, overheating can cause damage, first to color, such as undue darkening, and finally, to the extent of charring. The necessary and sufficient temperature and exposure time for expansion without such damage is a function of these two variables as well as the state of subdivision of the tobacco. Thus, to avoid undesirable damage in the heating step, the impregnated tobacco should not be exposed to the higher temperature levels, e.g. 370° C., than several tenths of a second.

One method for causing the expansion of the tobacco cells is to use the radiation methods described in either U.S. Pat. Nos. 3,409,022 or 3,409,027. Another method involves the use of a heat gun such as the Dayton heat gun or the equivalent, operating at an exit air temperature of 190°–344° C. for a period of about 0.2 second to 4 minutes, the shorter times, of course, being given for the higher temperatures. In this operation, the tobacco never attains a temperature above about 140° C., being cooled by the rapid evolution of gases. The presence of steam during heating assists in obtaining optimum results.

Another system, usually preferred, is to use a dispersion dryer, for example, one that is supplied either with steam alone or in combination with air. An example of such a dryer is a Proctor & Schwartz PB dispersion dryer. The temperature in the dryer may range from about 121° to 371° C. with contact time in the dryer of about 4 minutes at the lowest temperature to about 0.1 to 0.2 second at the highest temperature. In general, a 0.1 to 0.2 second contact time is utilized when the hot gas temperature is 260°–315° C. or somewhat higher. As stated before, other known types of heating means may be used as long as they are capable of causing the impregnated tobacco to expand without excessive darkening. It should be noted, that where a high percentage of oxygen is present in the hot gases, it will contribute to darkening, so that if a hot-steam mixture is employed, a high proportion (e.g., over 80% volume) of steam is preferred. The presence of a steam atmosphere of 20% or more of the total hot gas composition aids in obtaining the best expansion.

The present process may be conducted in various forms of apparatus specific embodiments of which will be described in detail later in this specification.

It is important that the apparatus in which the liquid carbon dioxide-containing tobacco is converted to solid carbon dioxide-containing tobacco is able to contain gases at elevated pressures, as high as 1000 psig or more. This vessel is preferably employed for the initial contact of the liquid carbon dioxide with the tobacco; however, such contact could be made in a separate vessel, if desired, and the liquid carbon dioxide-containing tobacco could then be placed in the pressure vessel. There may be numerous arrangements of the pressure vessel. However, there should preferably be a valved inlet from a source of liquid carbon dioxide and a valved outlet at the bottom of the vessel whereby liquid may be drained off; a second valved outlet near the top, for venting, may be added, and could be inserted as part of the inlet line, if desired, placed between the vessel and the inlet valve. A means of heating the vessel, such as external heating coils, is necessary. Supporting the vessel on a load cell greatly simplifies measuring the carbon dioxide charge. A supplementary vessel similarly equipped with weighing means and heating coils is advantageous, though not essential, because it permits preheating a charge of liquid carbon dioxide from its usual low storage temperature of $-20°$ C. (which may be about 215 psig). This arrangement helps to prevent the formation of solid carbon dioxide on charging the main vessel, and shortens the time the tobacco might be kept below the freezing point of its moisture. In operation, the filler may be placed in the main pressure vessel in a suitable holder such as a wire basket suspended above the bottom of the vessel. The closed vessel may then be purged with carbon dioxide gas and the outlets closed, then liquid carbon dioxide is introduced from storage, for example, at 250 psig, in an amount sufficient to cover all of the tobacco present in the vessel. The temperature is raised without delay, i.e., within 3 to 20 minutes by the heating means, e.g., heating coils to bring the tobacco to at least $-2°$ C. but less than $31°$ C. (the critical temperature of carbon dioxide) and this condition is preferably maintained for 1 to 20 minutes while impregnation takes place. Excess liquid carbon dioxide is then drained off by opening the lower outlet of the vessel to a suitable reservoir or the like disposal system, and when all excess liquid has been removed from the vessel, the vessel is vented to atmospheric pressure. The tobacco, which will now generally contain from about 5 to 25% of solid carbon dioxide by weight is then subjected to an operation to volatilize the solid carbon dioxide, preferably by removing the solid carbon dioxide-containing tobacco from the vessel and passing it through any of several rapid heating systems to achieve expansion. As indicated earlier in this specification, systems for this expansion process are most satisfactory which provide rapid, turbulent contact with the hot gas or vapor. With proper control of temperature and exposure time the product may be recovered in the expanded state at a desired moisture content such as 8 to 12% so that little or no reordering is required as it is with products from many expansion processes.

Representative embodiments of apparatus which can be used in the practice of the present invention are depicted in the drawing in which.

Throughout the following description like reference numerals are used to denote like parts in the drawing.

Figure 1:
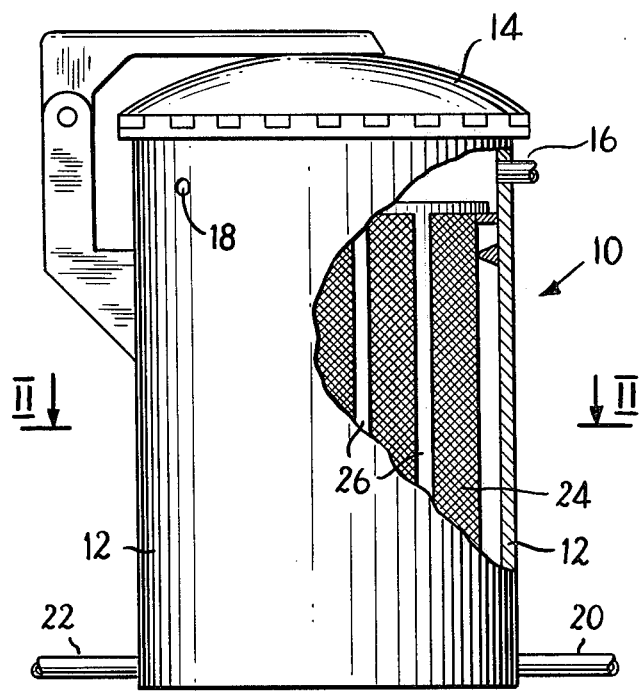
FIG. 1 is an elevational view with portions broken away of one form of apparatus in which tobacco can be expanded in accordance with the principles of the present invention.
Figure 2:
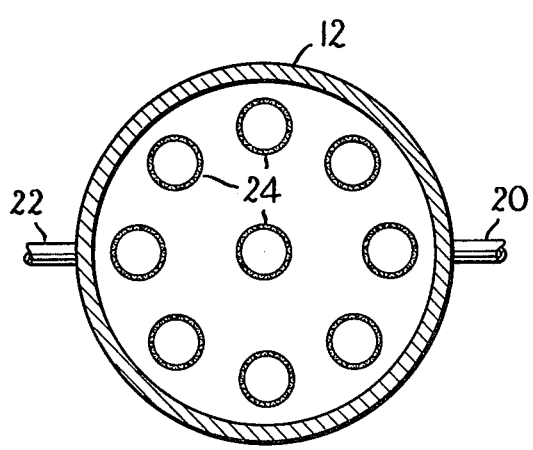
FIG. 2 is a sectional view as taken along the line II—II in FIG. 1.
Figure 3:
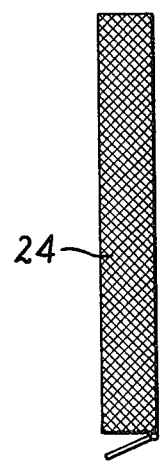
FIG. 3 is an elevational view of a wire basket in which tobacco can be received, the basket in turn being received within the apparatus shown in FIG. 1.

Referring now to FIGS. 1-3, there is depicted one form of apparatus 10 in which tobacco can be expanded in accordance with the principles of the present invention. The apparatus 10 includes a pressure vessel 12 fitted with a hinged cover 14 at the top, and provided further with ported connections 16 and 18 near the top as well as inlet and outlet lines 20 and 22 at the bottom which ported connections and lines allow for purging the interior of vessel 12 with a gaseous medium as well as introducing and removing liquid carbon dioxide therefrom. The tobacco to be expanded can be loaded in the cage members 24 (FIG. 3) and the cages 24 in turn are removably received in a suitable rack structure 26 within the vessel 12 in any convenient arrangement, as for example in the circular array depicted in FIG. 2. The cover 14 is then tightly closed on the vessel 12. The interior of the vessel then can be purged of any gaseous residue therein through the agency of gaseous carbon dioxide flow through inlet at line 20 and outlet through port 16. Line 20 and port 18 are then closed and the vessel filled with liquid carbon dioxide through line 16, the unit being filled until the tobacco contained in the cage 24 is completely immersed in the liquid carbon dioxide, line 16 then being closed. The pressure inside the vessel is then brought to a desired pressure range for example in the range of 450-850 psig. After a suitable soaking period, the liquid carbon dioxide is drained from the vessel (through line 22) and the interior of the vessel vented to atmosphere by opening port 18 to thus convert the liquid carbon dioxide remaining in the tobacco to a solid state. A steam and or hot air mixture is then circulated through line 22 with continuous venting through the port 18 to effect expansion of the tobacco. On completion of the expansion operation, cover 14 is opened and the tobacco removed for such further processing as may be desired.

Figure 4:
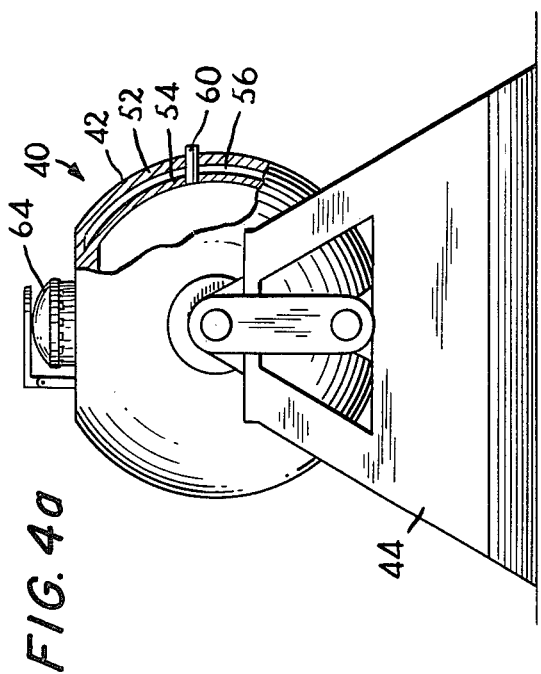
FIGS. 4 and 4a are respectively front and end elevational views and depict a somewhat different form of apparatus in which the pressure vessel is mounted for rotation about a fixed axis to facilitate intimate mixing of the liquid carbon dioxide and tobacco during impregnation as well as vaporization of the solid carbon dioxide during expansion of the tobacco.
Figure 4A:
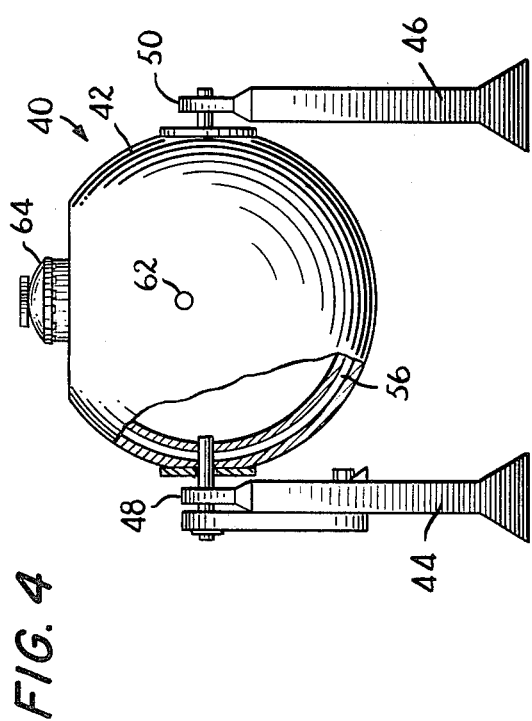

Another form of apparatus which can be used is shown in FIGS. 4 and 4a. The apparatus 40 includes a shell 42 showing an outer wall 52 and an inner wall 54 which define therebetween a jacketed chamber 56 in the pressure vessel. Further the pressure vessel 42 is journaled as at 48 and 50 on supports 44, 46 respectively for rotation about a fixed axis. Apparatus 40 also includes ports 60 and 62 provided for purging and liquid carbon dioxide filling purposes and a hinged cover 64. The jacketed chamber 56 is provided so that a heating medium can be circulated therethrough for maintaining the carbon dioxide in liquid form, e.g. at a temperature of about $-2°$ C. to about $31°$ C. Further the jacketed chamber is provided to facilitate the evaporation step and the rotatable mounting of the vessel allows for intimate mixing of the tobacco and liquid CO2 as well as enhancing vaporization by reason of the rotative movement causing the tobacco to contact the heated inner wall surface 54.

Figure 5:
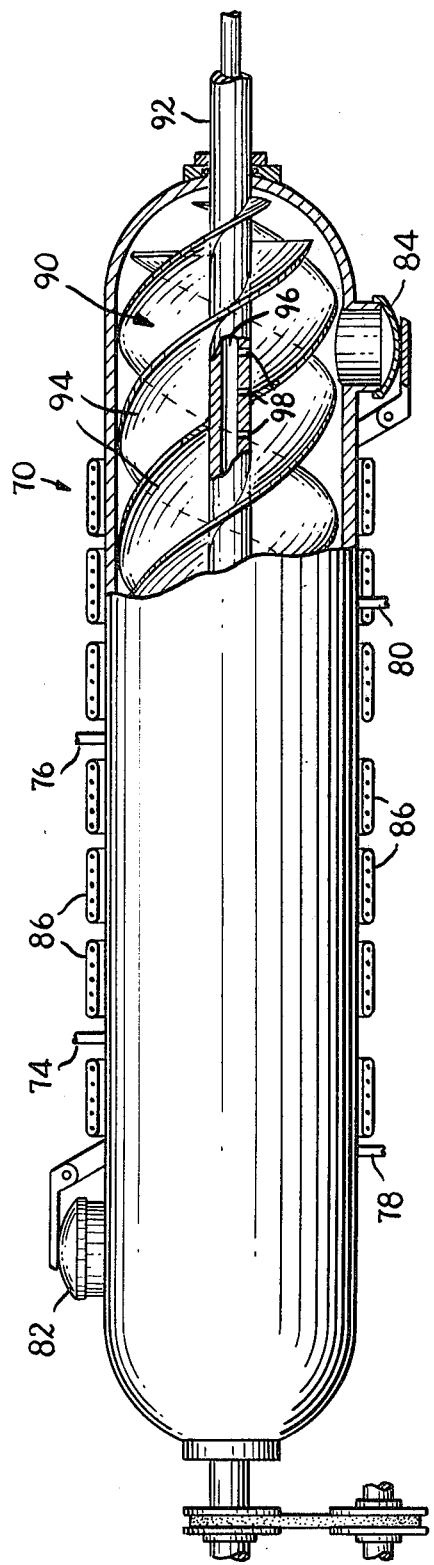
FIG. 5 is a further alternative form of apparatus in which a mixer unit is embodied in the pressure vessel to facilitate uniform distribution of the liquid carbon dioxide and intimate mixing thereof with the tobacco, the mixer shaft further being provided with a central passage and distribution ports for delivery of steam and or hot air therethrough during the expansion step.

FIG. 5 depicts a further form of apparatus 70 which includes an elongated preferably horizontally disposed pressure vessel 72 fitted with a number of ports 74, 76, 78, 80 used in connection with purging and liquid carbon dioxide supply and withdrawal, a filling hatch 82 and a withdrawal hatch 84 through which the tobacco can be moved from the vessel following expansion.

Externally disposed around the periphery of the pressure vessel 72 are a series of heating coils 86 which can be used in conjunction with raising the pressure of the liquid carbon dioxide but more particularly to maintain it at a temperature of between about $-2°$ C. and $31°$ C. during impregnation. The vessel 72 is also provided with mixing means 90 in the form of an elongated axially disposed shaft 92 carrying an arrangement of mixing vanes 94, with the shaft being provided further with a central passage 96 and a series of connected radially directed passages 98 communicating with the exterior surface of the shaft. Tobacco is introduced through filling hatch 82, and upon filling of the vessel with tobacco, the hatch is closed. The interior of the vessel 72 is then purged with gaseous carbon dioxide through ports 76 and 80. After purging liquid carbon dioxide is introduced through port 80 and until suitable pressure (for example 600 psig) is reached. The shaft 92 is then rotated to facilitate achieving intimate mixing of the tobacco and liquid carbon dioxide. After a suitable contact time the mixing is stopped and the liquid carbon dioxide is drained from the vessel through port 78 and following which the interior of the vessel is vented to atmosphere as through port 74 to convert the liquid carbon dioxide remaining in the tobacco to solid form. Steam and or hot air is then introduced through the central passage 92 and the radial branches 98 of the shaft to effect expansion of the tobacco. Further the shaft is rotated to facilitate contact of the impregnated tobacco with the steam and or hot air. Following the completion of the expansion operation, the tobacco is removed through hatch 84.

The following examples are illustrative:

EXAMPLE 1

Ten pounds of bright tobacco particles of normal filler size having a moisture content of about 12% by weight was placed in a wire cage and placed in a pressure vessel. The vessel was then purged by running carbon dioxide gas through it at room temperature for a period of three minutes, after which carbon dioxide liquid was introduced into the vessel from a pressure container, where it had been maintained at a pressure of about 200 psig and a temperature of about $-18°$ F. (i.e. $-28°$ C.). Sufficient liquid carbon dioxide was used to cover the tobacco sample. This comprised about 30 pounds of liquid carbon dioxide per pound of tobacco. The pressure in the vessel was then raised from 300 psig to about 700 psig by heating the vessel up to a temperature of $14°$ C. and this pressure was then maintained for about three minutes. Excess carbon dioxide liquid was removed from the tobacco by draining it off the tobacco, and the gas in the vessel was then vented rapidly from the vessel (vent time 45 seconds), whereby solid carbon dioxide was formed in the tobacco structure.

Two samples of treated tobacco were taken. The first sample (about five pounds) was heated in a tower with hot air at $220°$ C. The second (about five pounds) was heated in a tower with superheated steam at a temperature of $220°$ C.

In each the percentage of oven volatiles (% O.V.) was measured. This is a measure of the moisture content plus a minor fraction of other components and is determined as follows:

$$O.V.\% = \frac{\text{weight loss of sample after 3 hrs. at}}{\text{sample weight}} \, 100° \text{ C.}$$

The filling power of each sample was also determined, as cc/10 g by the following method: 10 g of filler is placed in a graduated cylinder and subjected to a known load of 1860 g. The volume after depression is measured as a reflection of the filling power of filler as used in cigarettes. A control consisting of 10 g of untreated tobacco particles taken from the same batch of bright tobacco particles as the pound of tobacco particles treated as described above.

The following results were obtained:

| Sample | Filling Power cc/10 grams | % O.V. | Corrected Filling Power at 12% O.V. |
|---|---|---|---|
| Control | 33 | 13.2 | 38 |
| 220° C. | 78 | 8.3 | 51 |
| Superheat Steam | 97 | 8.5 | 71 |

It will be seen from the above data that the expansion due to the vaporization of carbon dioxide was considerable and that the low loss in O.V. decreases the need for a reordering tobacco step prior to using it in a smoking product and that superheated seems necessary for best expansion.

EXAMPLE 2

Five pounds of bright tobacco filler having a moisture content of 12% by weight was impregnated with carbon dioxide liquid as described in Example 1. A two pound sample of the treated tobacco was expanded by a saturated steam flow (at $166°$ C.) as described in Example 1. One pound samples of the unexpanded filler (control) and carbon dioxide-expanded filler were evaluated for moisture (O.V.) as in Example 1. The results of the analysis are set forth below:

| Analysis | Control Sample | Test Sample Carbon Dioxide-Expanded |
|---|---|---|
| Moisture (O.V.) | 12.5% | 12.5% |
| Total Alkaloids* | 2.1% | 1.9% |
| Reducing Sugars* | 12.1% | 11.8% |

*Analysis by method described in "Tobacco Science", Vol. 13, pp. 13–15 (1969)

It will be seen that the carbon dioxide-expanded filler shows little change from the control, and that the original composition of the tobacco is essentially preserved during the expansion process.

EXAMPLE 3

A series of 10 pound samples of bright tobacco filler having a moisture content of 12% by weight was impregnated with carbon dioxide liquid as described in Example 1 at pressures that varied from 400 to 900 psig. The impregnated filler was heated in a tower with superheated steam at 270° C.

The following results were obtained:

| Pressure | % O.V. | Filling Power cc/10 grams | Corrected Filling Power at 12% O.V. |
|---|---|---|---|
| 400 | 8.9 | 61.1 | 43.3 |
| 500 | 8.6 | 69.3 | 45.9 |
| 600 | 6.4 | 104.5 | 65.4 |
| 700 | 6.0 | 114.8 | 68.0 |
| 800 | 6.5 | 130.8 | 72.5 |
| 900 | 6.4 | 130.9 | 71.2 |

It can be seen that in order to obtain optimum product the pressure during impregnation should be above 600 psig and preferentially above 700 psig.

EXAMPLE 4

Another series of bright tobacco samples were impregnated as in Example 1. The vent time (time of gaseous pressure release) was gradually increased from 49 seconds to 420 seconds. The impregnated filler was heated in a tower by superheated steam at 525° F. (270° C.). The results are listed below:

| Vent Time Seconds | % O.V. | Filling Power at Tower Exit O.V. cc/10 grams | Corrected Filling Power at 12% O.V. |
|---|---|---|---|
| 49 | 3.8 | 121.2 | 65.5 (±3.6) |
| 65 | 4.0 | 116.5 | 69.2 |
| 148 | 4.1 | 95.9 | 60.0 |
| 195 | 4.4 | 112.7 | 72.1 |
| 247 | 4.2 | 101.4 | 61.6 |
| 420 | 4.6 | 116.7 | 67.7 |

The results indicate that the rate of pressure release does not affect product quality.

EXAMPLE 5

A third series of bright tobacco filler samples was impregnated as in Example 1. The soak times (time of contact of the filler with the carbon dioxide liquid) were varied from 60 seconds to 869 seconds. The impregnated filler was heated in a tower with superheated steam at 525° F. (270° C.) at a gas velocity of 100 feet/second.

The following results were obtained:

| Soak Time Seconds | % O.V. | Filling Power at Tower Exit O.V. cc/10 grams | Corrected Filling Power at 12% O.V. |
|---|---|---|---|
| 60 | 3.5 | 109.3 | 59.7 |
| 180 | 4.2 | 110.0 | 62.1 |
| 300 | 3.0 | 112.1 | 60.0 |
| 600 | 3.2 | 117.3 | 62.2 |
| 869 | 3.6 | 111.4 | 60.9 |

It can be seen from the above data that the expansion of the carbon dioxide impregnated filler is not changed by the length of contact with carbon dioxide liquid during the impregnation step.

In another series, input moistures were varied from 8% to 19% O.V.—and the filler was impregnated as in Example 1. The impregnated filler was heated in a tower at 240° C. gas velocity of 100 feet/second in a saturated steam atmosphere.

The following results were obtained:

| Input % O.V. | Filling Power cc/10 grams | % O.V. | CV Correct to 12% O.V. cc/10 grams |
|---|---|---|---|
| 8.0 | 57.1 | 5.8 | 37.2 |
| 11.5 | 97.7 | 7.4 | 63.6 |
| 13.4 | 127.6 | 7.8 | 67.3 |
| 16.5 | 124.9 | 7.6 | 71.2 |
| 17.2 | 115.4 | 8.0 | 73.2 |
| 19.0 | 93.3 | 9.6 | 67.3 |

The results indicate that the input moisture of filler should be above 8% and that the moistures of 13–19% are beneficial for good expansion with good tower exit moisture so that less "reordering" (rehumidification) is required.

The following experiment was also conducted.

EXPERIMENT 1

One pound of 12% O.V. bright cut filler was impregnated with carbon dioxide gas at a pressure of 900 psig. After an equilibration time of 10 minutes the gas was vented to the atmosphere and the sample was removed. A portion of the filler was heated at 66° C. in a low velocity air stream. A second portion was allowed to come to ambient temperature conditions (21° C.). The results are listed below:

| | Temperature | Filling Power, cc/10 grams |
|---|---|---|
| Sample 1 | 66° C. | 37 |
| Sample 2 | 21° C. | 34 |
| Control | — | 32 |

The results indicate that the immersion of the filler in the carbon dioxide liquid seems necessary and that the entrapment of carbon dioxide under pressure followed by the pressure release does not exert sufficient force to effect expansion.

What is claimed is:

1. A process for expanding tobacco comprising the steps of (1) contacting tobacco with liquid carbon dioxide under conditions such that the temperature of the tobacco is maintained at a level no lower than about −2° C. and such that substantially all of the liquid carbon dioxide is maintained in liquid form to impregnate the tobacco with the liquid carbon dioxide, (2) subjecting the liquid carbon dioxide-impregnated tobacco to conditions such that the liquid carbon dioxide is converted to solid carbon dioxide and (3) thereafter subjecting the solid carbon dioxide-containing tobacco to conditions whereby the solid carbon dioxide is vaporized to cause expansion of the tobacco.

2. A process for expanding tobacco comprising the steps of (1) contacting tobacco containing from about 8 to about 50% by weight of water with at least 1 part, by weight per part of tobacco, of liquid carbon dioxide under conditions such that the temperature of the tobacco during impregnation is maintained at a level no lower than about −2° C. and such that all of the liquid carbon dioxide is maintained in liquid form to impregnate the tobacco with the liquid carbon dioxide, (2) subjecting the liquid carbon dioxide-impregnated tobacco to conditions such that the liquid carbon dioxide is converted to solid carbon dioxide to provide an impregnated tobacco, and (3) thereafter subjecting the solid carbon dioxide-containing tobacco to conditions whereby the solid carbon dioxide is vaporized to cause expansion of the tobacco.

3. A process for expanding tobacco comprising the steps of (1) contacting tobacco containing from about 8 to about 50% by weight of water with at least 1 part by weight, per part of tobacco, of liquid carbon dioxide, maintaining during said contact, a pressure of from about 583 to about 983 PSIG and a temperature of from about 5° to 24° C. for a period of from about 0.5 to 10 minutes, such that substantially all of said liquid carbon dioxide is maintained in liquid form whereby said tobacco is impregnated with said liquid carbon dioxide, (2) subjecting the liquid carbon dioxide-impregnated tobacco to conditions such that the liquid carbon dioxide is converted to solid carbon dioxide and (3) thereafter subjecting the solid carbon dioxide-containing tobacco to a pressure of from about 0 to about 10 PSIG and a temperature of from about 100° to 360° C. for a period of from about 0.2 to 10 seconds, whereby the solid carbon dioxide is vaporized to cause expansion of the tobacco.

4. A process as in claim 3 where about 5 to about 10 parts by weight liquid carbon dioxide is used per part of tobacco.

5. Apparatus for expanding tobacco which comprises a pressure vessel,
means for introducing and withdrawing tobacco from said pressure vessel,
means for introducing liquid carbon dioxide into said pressure vessel to impregnate said tobacco therewith,
means for withdrawing said liquid carbon dioxide from said pressure vessel, following impregnating of said tobacco,
means for maintaining said carbon dioxide at predetermined temperature and pressure in said pressure vessel whereby it remains in liquid state,
means for converting the liquid carbon dioxide impregnating said tobacco to solid carbon dioxide, and
means for vaporizing the solid carbon dioxide impregnating said tobacco to effect expansion of said tobacco.

6. The apparatus of claim 1 in which the means for maintaining said carbon dioxide in liquid state includes heating means effective to maintain said liquid carbon dioxide at a temperature of between about −2° C. and 31° C.

7. The apparatus of claim 6 in which the means for converting the liquid carbon dioxide impregnating said tobacco to solid carbon dioxide includes means to vent the interior of said vessel to atmosphere.

8. The apparatus of claim 6 further comprising means for purging the interior of said pressure vessel with a gaseous purging agent to remove undesirable gaseous residue therefrom.

9. The apparatus of claim 6 further comprising a plurality of tobacco receivable receptables, and means in said vessel for removably receiving said receptables in said vessel.

10. The apparatus of claim 6 in which said pressure vessel has inner and outer walls defining a jacketed structure therebetween, means for vaporizing said solid carbon dioxide comprising a heated medium circulated in said jacket.

11. The apparatus of claim 1 in which said pressure vessel is rotatably supported for rotation about a fixed axis whereby said vessel can be rotated to intimately mix said liquid carbon dioxide with said tobacco and during the vaporization of said solid carbon dioxide to facilitate contact of said tobacco with said inner wall.

12. The apparatus of claim 7 in which said heating means comprises heating coils disposed exteriorly on said pressure vessel.

13. The apparatus of claim 6 in which said pressure vessel is an elongated structure, there further being provided mixing means within said pressure vessel operable to effect intimate mixing of said liquid carbon dioxide with said tobacco and in cooperation with said vaporizing means to facilitate expansion of said tobacco.

14. The apparatus of claim 1 in which said mixing means comprises an elongated shaft extending interiorly of and rotatably within said pressure vessel, said shaft being fitted with mixing vanes fixed thereto.

15. The apparatus of claim 1 in which said shaft is provided with an axial directed passage and radial branches opening at the surface of said shaft through which a heating medium can be flowed into contact with said tobacco to effect vaporization of said solid carbon dioxide.

16. The method of expanding tobacco which comprises the steps of (1) impregnating the tobacco with liquid carbon dioxide under conditions such that substantially all of the liquid carbon dioxide is maintained in liquid form to impregnate the tobacco with the liquid carbon dioxide, (2) subjecting the liquid carbon dioxide-impregnated tobacco to conditions such that the liquid carbon dioxide is converted to solid carbon dioxide and (3) thereafter subjecting the solid carbon dioxide-containing tobacco to conditions whereby the solid carbon dioxide is vaporized to cause expansion of the tobacco.

17. Apparatus for expanding tobacco which comprises a pressure vessel,
means for introducing and withdrawing tobacco from said pressure vessel,
means for introducing liquid carbon dioxide into said pressure vessel to impregnate said tobacco therewith,
means for withdrawing said liquid carbon dioxide from said pressure vessel, following impregnating of said tobacco,
means for maintaining said carbon dioxide at predetermined temperature and at a pressure approximately between 230 and 915 p.s.i.a. in said pressure vessel whereby it remains in liquid state,
means for converting the liquid carbon dioxide impregnating said tobacco to solid carbon dioxide, and
means for vaporizing the solid carbon dioxide impregnating said tobacco to effect expansion of said tobacco.

* * * * *